United States Patent [19]

Lee et al.

[11] Patent Number: 5,783,217
[45] Date of Patent: Jul. 21, 1998

[54] LOW TEMPERATURE CALCIUM PHOSPHATE APATITE AND A METHOD OF ITS MANUFACTURE

[75] Inventors: Dosuk D. Lee, Brookline, Mass.; Christian Rey, Castanet, France; Maria Aiolova, Brookline; Ali Tofighi, Belmont, both of Mass.

[73] Assignee: Etex Corporation, Cambridge, Mass.

[21] Appl. No.: 554,817

[22] Filed: Nov. 7, 1995

[51] Int. Cl.$^6$ .......................... A61K 33/42; C01B 25/32
[52] U.S. Cl. .................... 424/602; 264/234; 423/308; 423/311; 428/704; 514/2
[58] Field of Search ..................... 423/308, 309, 423/311; 264/16, 19, 234; 424/602; 428/704; 514/2

[56] References Cited

U.S. PATENT DOCUMENTS

| | | |
|---|---|---|
| Re. 33,221 | 5/1990 | Brown et al. |
| 4,612,053 | 9/1986 | Brown et al. |
| 4,849,193 | 7/1989 | Palmer et al. |
| 4,880,610 | 11/1989 | Constantz |
| 4,938,938 | 7/1990 | Ewers et al. |
| 5,037,639 | 8/1991 | Tung |
| 5,053,212 | 10/1991 | Constantz et al. |
| 5,149,368 | 9/1992 | Liu et al. |
| 5,178,845 | 1/1993 | Constantz et al. |
| 5,427,754 | 6/1995 | Nagata et al. ............ 423/308 |
| 5,470,803 | 11/1995 | Bonfield et al. |
| 5,522,893 | 6/1996 | Chow et al. ............ 623/11 |
| 5,525,148 | 6/1996 | Chow et al. ............ 106/35 |
| 5,650,176 | 7/1997 | Lee et al. ............ 423/308 |

OTHER PUBLICATIONS

Bezic et al. "Electron Probe Microanalysis of Noncarious Enamel and Dentin and Calcified Tissues in Mottled Teeth" *J Dent Res.* 48(1), 131–139 (Jan.–Feb., 1969).

Constantz et al. "Skeletal Repair by in Situ Formation of the Mineral Phase of Bone" *Science* 267, 1796–99 (Mar. 1995).

Glimcher, M.J., "Recent studies of the mineral phase in bone and its possible linkage to the organic matrix by protein-bound phosphate bonds" *Phil. Trans. R. Soc. Londs.* B 304, 479–508 (1984).

Greenfield et al., "Formation Chemistry of Amorphous Calcium Phosphates Prepared from Carbonate Containing Solutions" *Calc. Tiss. Res.* 9, 152–162 (1972).

Holmes et al. "Surface Areas by Gas Adsorption on Amorphous Calcium Phosphate and Crystalline Hydroxyapatite" *Calc. Tiss. Res.* 7, 163–74 (1971).

Labarthe et al. "Sur la Structure et les Proprietes des Apatites Carbonatees de Type B Phospho–Calciques" *Ann. Chim.* 8 (5), 289–301 (1973).

Nylen et al., "Molecular and Ultrastructural Studies of Non–Crystalline Calcium Phosphates" *Calc. Tiss. Res.* 9, 95–108, (1972).

Pool, R. "Coral Chemistry Leads to Human Bone Repair" *Science* 267, 1772 (1995).

Rey et al. "The Carbonate Environment in Bone Mineral: A Resolution–Enhanced Fourier Transform Infrared Spectroscopy Study" *Calcif. Tissue Int.* 45, 157–164 (1989).

Rey et al. "Structural Studies of the Mineral Phase of Calcifying Cartilage" *Jrnal of Bone and Mineral Research* 6 (5), 515–525 (1991).

Rey et al. "Preparation of Microporous Ceramic at Low Temperature from Poorly Crystalline Apatite" Materials Research Society Symposium V, San Francisco (1993).

Tung et al. "An Intermediate State in Hydrolysis of Amorphous Calcium Phosphate" *Calcif. Tissue Int.* 35, 783–790 (1983).

*Primary Examiner*—Wayne Langel
*Attorney, Agent, or Firm*—Choate, Hall & Stewart

[57] ABSTRACT

A method of preparing a low crystallinity calcium phosphate apatite is described in which a low crystallinity calcium phosphate is precipitated from an aqueous solution comprising calcium and phosphate ions; collected from the solution; and dehydrated in a humidity and at a temperature selected to minimize growth and promote conversion to calcium phosphate apatite. The resultant calcium phosphate apatite is block solid of improved strength, porosity and bioresorbability.

41 Claims, 3 Drawing Sheets

LOW TEMPERATURE CALCIUM PHOSPHATE APATITE AND A METHOD OF ITS MANUFACTURE

FIELD OF THE INVENTION

This invention relates to a synthetic calcium phosphate apatite having a variety of uses including as a human or animal implant material. The invention further relates to a calcium phosphate apatite of high mechanical strength and porosity.

BACKGROUND OF THE INVENTION

Calcium phosphates are the principal constituent of hard tissues (bone, cartilage, tooth enamel and dentine). Naturally-occurring bone mineral is made of nanometer-sized, low crystalline calcium phosphate with a hydroxyapatite structure. However, unlike the ideal stoichiometric crystalline hydroxyapatite, $Ca_{10}(PO_4)_6(OH)_2$, with an atomic Ca/P ratio of 1.67, the composition of bone mineral is significantly different and may be represented by the following formula,

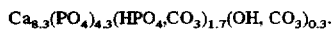

$Ca_{8.3}(PO_4)_{4.3}(HPO_4,CO_3)_{1.7}(OH, CO_3)_{0.3}$.

Bone mineral non-stoichiometry is primarily due to the presence of divalent ions, such as $CO_3^{2-}$ and $HPO_4^{2-}$, which are substituted for the trivalent $PO_4^{3-}$ ions. Substitution by $HPO_4^{2-}$ and $CO_3^{2-}$ ions produces a change of the Ca/P ratio, resulting in Ca/P ratio which may vary between 1.50 and 1.70, depending largely on the age and bony site. Generally, the Ca/P ratio increases during aging of bone, suggesting that the amount of carbonate species typically increases for older bones.

It is the Ca/P ratio in conjunction with nanocrystalline size and the low crystallinity nature that yields specific solubility property of the bone minerals. And because bone tissues undergo constant tissue repair regulated by the mineral-resorbing cells (osteoclasts) and mineral-producing cells (osteoblasts), solubility behavior of minerals is important in maintaining a delicate metabolic balance between these cell activities.

Synthetic bone graft material made to closely resemble natural bone minerals can be a useful replacement for natural bone. Acceptable synthetic bone can avoid the problem of availability and harvesting of autogenous bone (patient's own bone) and the risks and complications associated with allograft bone (bone from a cadaver), such as risks of viral transmission. Consequently, there has been considerable attempts to synthesize a ceramic material which closely resembles natural bone for use as implants. Hydroxyapatite is the preferred choice because, although it is a stoichiometric, crystalline form with generally larger crystal sizes, is chemically closest to the naturally occurring mineral in bone.

An ideal synthetic bone graft desirably possesses the following properties: (1) it should be chemically biocompatible like hydroxyapatite; (2) it should provide some degree of structural integrity in order to keep the graft in place and intact until the patient's own bone heals around it; (3) it should be a soluble form to permit resorption so that the patient's own bone replace the foreign bone graft; and, because it may be necessary to incorporate biomolecules, such as bone growth proteins that can stimulate bone-forming osteoblast cells, into the synthetic bone material, (4) it is desirable that the process used to form the material be carried out at low temperatures. Most bone growth proteins (such as Bone Morphogenetic Proteins) are heat sensitive and lose their bioactivity at temperatures exceeding body temperatures.

Fulfillment of these properties may be met by a calcium phosphate apatite material in which parameters, such as Ca/P ratios, crystal size, crystallinity, porosity, density, thermal stability and material purity, are controlled.

LeGeros R. Z. in *Calcium Phosphates in Oral Biology and Medicine* (Karger Pub. Co., New York 1991) teaches that a highly crystalline form of hydroxyapatite is produced by solution precipitation followed by sintering at high temperatures (800°–1200° C.). High temperature treatment yields highly stoichiometric hydroxyapatite with crystal sizes on the order of several microns with Ca/P of 1.67. Such highly crystalline hydroxyapatite has an extremely low solubility rendering it essentially insoluble in the host tissue. Therefore, it is not replaced by living bone tissue and it remains in the patient for an undesirably extended period.

Hydroxyapatite also is produced by a solid-state acid-base reaction of primarily crystalline calcium phosphate reactants. Such an approach results in materials that are sometimes poorly reacted, inhomogeneous and which have a significant crystalline hydroxyapatite content.

Constantz in U.S. Pat. No. 4,880,610 reports on the preparation of calcium phosphate minerals by the reaction of a highly concentrated phosphoric acid with a calcium source in the presence of a base and hydroxyapatite crystals. The resultant product is a polycrystalline material containing a crystalline form of hydroxyapatite minerals. Likewise, U.S. Pat. No. 5,053,212 to Constantz et al. discloses the use of a powdered acid source to improve the workability and mixability of the acid/base mixture; however, a mixed-phase calcium phosphate material similar to that of U.S. Pat. No. 4,880,610 is reported. Recently, Constantz et al. reported in *Science* (Vol. 267, pp. 1796–9 (24 March, 1995)) the formation of a carbonated apatite from the reaction of mono-calcium phosphate monohydrate, β- tricalcium phosphate, α-tricalcium phosphate, and calcium carbonate in a sodium phosphate solution, to provide a calcium phosphate material which is still substantially more crystalline in character than naturally occurring bone minerals. Similarly, Brown et al in U.S. Reissue Pat. No. 33,221 report on the reaction of crystalline tetracalcium phosphate (Ca/P of 2.0) with acidic calcium phosphates. Liu et al. in U.S. Pat. No. 5,149,368 discloses the reaction of crystalline calcium phosphate salts with an acidic citrate.

All of these references disclose a reaction of crystalline solids of calcium phosphate resulting in a crystalline form of hydroxyapatite solids. There has been little reported on the preparation of amorphous or low crystallinity hydroxyapatite block solids because the amorphous calcium phosphates used in the preparation of such are the least understood solids among the calcium phosphates and because the conventional amorphous calcium phosphate is largely considered to be inert and non-reactive solid.

The only mention of low crystallinity calcium phosphate material in the prior art has focused on the use of the amorphous calcium phosphate as a direct precursor to the formation of a highly crystalline hydroxyapatite compounds under generally high temperature conditions. Such a highly crystalline material is inappropriate for synthetic bone because it is highly insoluble under physiological conditions.

For example, Palmer et al. in U.S. Pat. No. 4,849,193 report the formation of crystalline hydroxyapatite powder by reacting an acidic calcium phosphate solution with a calcium hydroxide solution, with both solutions near saturation, so as to form an amorphous hydroxyapatite precipitate powder. The amorphous powder is then immediately dried and sintered at a high temperature between 700°–1100° C. to obtain a very high crystalline hydroxyapatite. Brown et al. in U.S. Reissue Pat. No. 33,221 report on the formation of crystalline hydroxyapatite for dental cement by reacting an amorphous phase of tetracalcium phosphate (Ca/P of 2.0) with at least one of the more acidic (crystalline) calcium phosphates. Tung in U.S. Pat. No. 5,037,639 discloses the use and application of standard amorphous calcium phosphate paste for the remineralization of teeth. Tung proposes the use of standard inert amorphous calcium phosphate mixed with and delivered as a chewing gum, mouth rinse or toothpaste, which converts to crystalline fluoride-containing hydroxyapatite upon entering oral fluids, which is useful to remineralize tooth enamel. Simkiss in PCT/GB93/01519 describes the use of inhibitors, such as $Mg^{2+}$ ions or pyrophosphate, which is mixed with amorphous calcium phosphate, and implanted into living tissues. Upon leaching of the inhibitors, for example $Mg^{2+}$ ions, into surrounding bodily fluids, the amorphous calcium-magnesium phosphate converts into crystalline hydroxyapatite.

In addition to providing a low crystallinity calcium phosphate apatite which mimics the properties of natural bone, it also may be desirable to obtain the material in the form of a high strength ceramic block. Such a block could be shaped or machined into any desired geometry. Typically, methods to obtain solid block hydroxyapatite involve pressing a powdered material into a densified block under heat and pressure. Such a pressed powder block is not of high strength and the application of heat to improve the mechanical properties of the material may change the chemical composition of the material, degree of crystallinity and/or have other adverse effects, particularly where proteins or other heat sensitive components are present. None of the procedures described hereinabove are capable of providing such a hydroxyapatite material directly from the preparation step and without an additional pressing step.

There remains a need to develop new synthetic bone material that more closely mimics the properties of naturally-occurring minerals in bone. In particular, there remains a need to provide synthetic bone materials which are completely bioresorbable, low crystallinity, nanometer-sized crystals which can be formed at low temperatures. Further, there remains a need to provide a ceramic hydroxyapatite of high strength and porosity which can be obtained from the manufacturing process in block form and which can be formed into the desired shape.

SUMMARY OF THE INVENTION

It is the object of the present invention to provide a calcium phosphate apatite material which is readily bioresorbable and of low crystallinity. It is a further object of the present invention to provide such a calcium phosphate apatite in powder or block form.

It is the object of the present invention to provide a low crystallinity calcium phosphate apatite solid with a surface that mimics the surface reactivity of naturally- occurring bone mineral.

It is another object of the present invention to provide a low crystallinity calcium phosphate apatite material and a method of its manufacture as a high strength block which can be readily machined into the desired geometry.

In one aspect of the invention, a low crystallinity calcium phosphate apatite is prepared by precipitating a low crystallinity calcium phosphate from an aqueous solution comprising calcium and phosphate ions; collecting the low crystallinity calcium phosphate from the solution; and dehydrating the low crystallinity calcium phosphate in a relative humidity and at a temperature selected to minimize crystal growth and to promote conversion to calcium phosphate apatite.

The calcium phosphate apatite of the present invention possesses an apatite structure and is related in structure and composition to hydroxyapatite. However, the calcium phosphate apatite of the present invention preferably includes carbonate and pyrophosphate ligands which more closely resembles naturally occurring bone. Further, the hydroxy content in the calcium phosphate apatite may vary from proportions found in hydroxyapatite to substantially absent.

By "low crystallinity" material it is meant a material that is amorphous having little or no long range order and/or a material that is nanocrystalline exhibiting crystalline domains on the order of nanometers or Angstroms.

In preferred embodiments, the low crystallinity calcium phosphate is cast into a mold before dehydration. In other preferred embodiments, the aqueous solution is selected to provide a calcium to phosphate ratio in the range of about 1.3 to 1.7, and preferably in the range of about 1.5 to 1.68. The precipitation may be carried out an aqueous solution additionally including carbonate ions. In yet another preferred embodiment, the aqueous solution is at a pH in the range of about 6.0 to about 8.5, and preferably in the range of about 7.3 to about 7.5. The calcium and phosphate ions may be introduced into the aqueous solution by fast addition, such as by way of example titration. In another preferred embodiment, the step of collection is selected from the group consisting of filtration, centrifugation and sedimentation.

In yet another preferred embodiment, the aqueous solution additionally includes a crystallization inhibitor. The inhibitor may be present in a range of about 0.5 wt % to about 30 wt % total dry weight of calcium and phosphate ion sources. The inhibitor is selected from the group consisting of carbonate ions, magnesium ion, and pyrophosphate ions.

In yet another embodiment of the present invention, the low crystallinity calcium phosphate is matured in solution prior to collection. The maturation is carried out for a time sufficient to obtain a calcium phosphate having a composition substantially similar to child's bone, adult bone or elderly bone, as desired. In preferred embodiments, the maturation time is in the range of about one hour to about one year, and preferably about two weeks to about six months.

By "maturation" as that term is used herein it is meant a process in which a precursor calcium phosphate is maintained in contact with an aqueous solution for a time to affect any of a number of characteristics of the calcium phosphate, including, but not limited to, reactivity, composition, degree of crystallinity and crystal domain size.

In yet another preferred embodiment, the step of dehydration is carried out at a temperature in the range of about 1° C. to about 50° C., and preferably in the range of about 4° C. to about 37° C. Dehydration is carried out preferably in a humidity controlled to within the range of about 55% to about 99% RH at a selected temperature, and preferably, within the range of about 60% to about 70% RH at 25° C. Dehydration is carried out for a time in the range of about one week to about one year, and preferably for a time in the range of about two weeks to about six months and more preferably for a time in the range of about three weeks to about four weeks.

In yet another embodiment of the invention, a bioactive molecule, such as a bone regenerating protein or an antibiotic, may be incorporated into the calcium phosphate apatite. The bioactive molecule may be introduced into the aqueous solution or into the collected precipitate before dehydration.

In yet another aspect of the invention, a low crystallinity calcium phosphate apatite is prepared by precipitating a low crystallinity calcium phosphate from an aqueous solution comprising calcium and phosphate ions; collecting the low crystallinity calcium phosphate from the solution; and lyophilizing the collected precipitate to minimize crystal growth and to promote conversion to calcium phosphate apatite.

In yet another aspect of the invention, a low crystallinity calcium phosphate apatite is provided as a solid block material having a porosity in the range of about 30 Å to about 100 Å and a hardness in the range of about 20 VHN to about 40 VHN.

By "block solid" as that term is used herein it is meant that the product is obtained as a single cake or piece, as compared to a powdered or granular solid.

BRIEF DESCRIPTION OF THE DRAWINGS

A description of the invention is made with reference to the Drawing, in which.

DETAILED DESCRIPTION OF THE INVENTION

Figure 1:
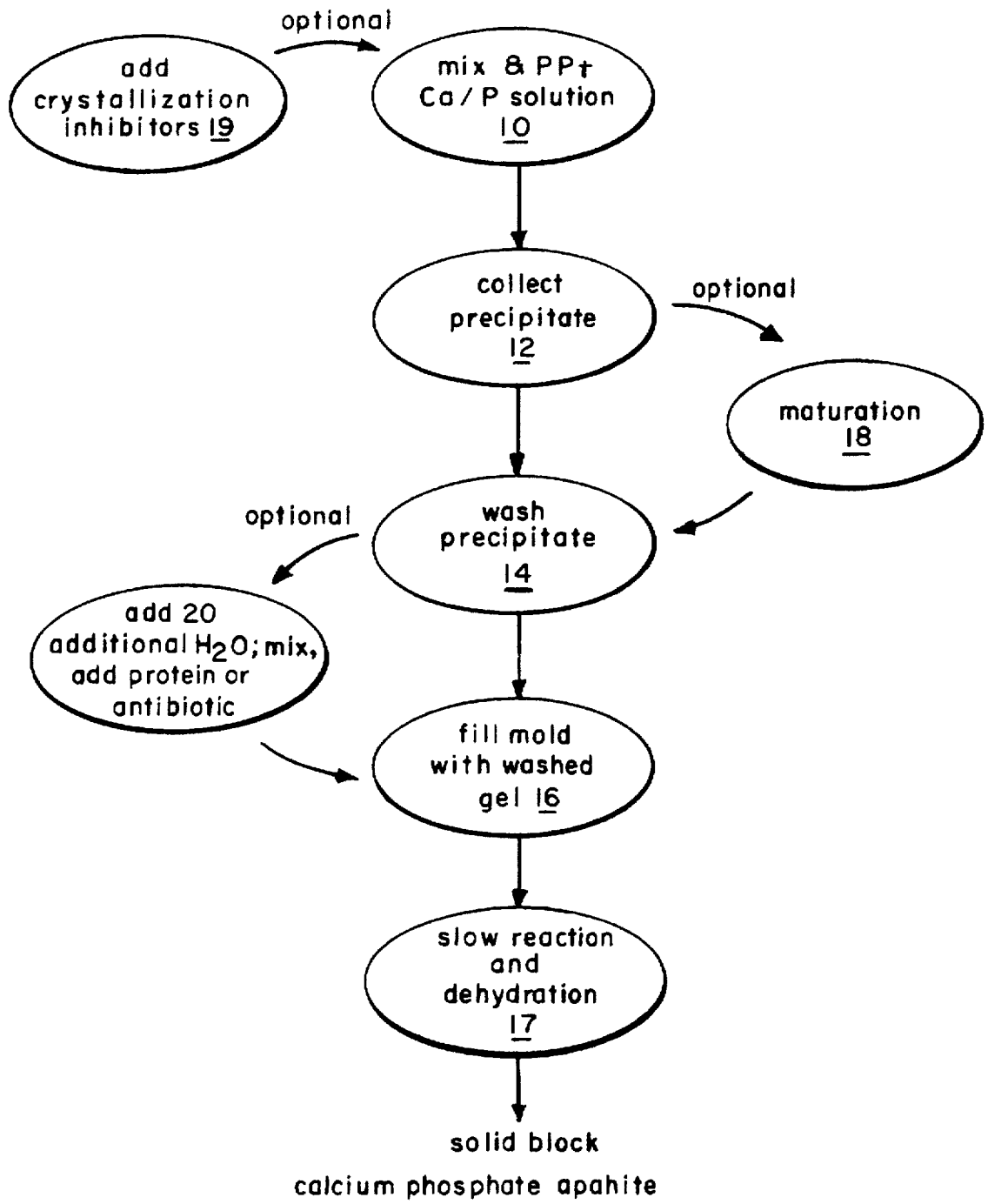
FIG. 1 is a block diagram illustrating a method of the invention.

The present invention provides a novel process for preparing a low crystallinity calcium phosphate apatite material which is highly bioresorbable. The calcium phosphate apatite may be prepared as a fine powder or as a block solid of high mechanical strength. The process of the present invention converts low crystallinity calcium phosphate into a low crystallinity calcium phosphate apatite block solid with careful control of pore size, porosity, composition and crystallinity. The method includes precipitation and collection of a low crystallinity calcium phosphate, followed by controlled reaction and dehydration in order to control the crystal size, strength and microporosity of the resultant calcium phosphate apatite ceramic solid. The method also includes precipitation and collection of a low crystallinity calcium phosphate, followed by lyophilization to control the particle size, crystallinity and microporosity of a resultant calcium phosphate apatite powder. Importantly, the process may be carried out at low temperatures, including ambient and sub-ambient temperatures.

The method of the present invention also permits modification of the chemical composition, thereby providing a further mode of controlling bioactivity of the product nanocrystalline calcium phosphate apatite. The bioactivity of the synthetic bone graft material of the present invention is enhanced relative to standard crystalline calcium phosphate apatite due to its controlled solubility in the patient. Desirably, a bone graft of low crystallinity calcium phosphate apatite is capable of resorbing at an optimum rate for bone to grow in and replace it. The solubility of low crystallinity calcium phosphate apatite can be varied by modifying the Ca/P chemical composition and/or the nanosized crystal microstructure, which can be controlled as described herein. In general, low crystallinity solids are more soluble than the comparable crystalline solid. By being able to control the solubility of the final product used as bone graft material, one can design the composition of the material to bio-correspond for younger, older or different bony site applications.

The method of the invention is described with reference to the flow diagram of FIG. 1. Precipitation of a calcium phosphate is performed by double decomposition between a calcium salt and a phosphate salt in an aqueous solution at low temperature (0° to 40° C.) as shown in step 10 of FIG. 1. The reaction is carried out at a pH which promotes rapid reaction and precipitation of the calcium phosphate. Typical pH values are in the range of about 6.5 to about 8.5, and more preferably in a range of about 7.3 to about 7.5. The precipitation may additionally include a carbonate ion source. The carbonate ion is useful in precipitation of calcium phosphates have various Ca/P ratios since carbonate ion occupies sites otherwise populated by phosphate ion, thereby reducing the phosphate content of the precipitate. Incorporation of carbonate ligands into the apatite structure is useful in preparing a material more closely mimicking natural bone. The carbonate ion may also serve as a crystallization inhibitor (see, below). Thus, by controlling the relative amounts of calcium, phosphate and carbonate in the precipitation solution, the final composition of the material may be controlled. Calcium to phosphate ratios in the range of 1.3 to about 1.7 are preferred. It is particularly preferred to have a Ca/P ratio of about 1.67 stoichiometric hydroxyapatite.

Low crystallinity in the precipitate may be obtained by controlling the rate and duration of the precipitation process. Low crystallinity includes both amorphous and nanocrystalline structures. The low crystallinity calcium phosphate is precipitated from solution under conditions where initial precipitation is rapid. Rapid precipitation results in the formation of many extremely small calcium phosphate nuclei. Additionally, rapid crystal or grain growth leads to the production of more defects within each grain, thereby also increasing solubility. The rapidly forming precipitates are nanocrystalline and very rich in labile phosphate (and carbonate) environments which give them a very high surface reactivity. At the extreme end of the spectrum, crystal or grain growth is so rapid and defect density is so significant that an amorphous calcium phosphate results. These materials have no long range structure, but are homogeneous when measured on an Angstrom scale. The compositions of the nanocrystalline and amorphous precipitates seem very similar and do not vary strongly with different precipitation conditions.

By "labile surface" as that term is used herein it is meant that the surface of the material or particle is reactive and capable of reacting with neighboring surfaces or materials to change chemical composition, crystallinity and crystal domain size of the material.

The thermodynamically favored crystalline form of calcium phosphate apatite is enhanced by reducing the rate of reaction. Therefore, steps may be taken to increase the rate of reaction to insure that an amorphous or nanocrystalline precipitate is obtained. Rapid mixture of calcium and phosphate sources favors formation of non-stable phases as a product. Allowing more reaction time for each ions to juxtaposition correctly to form a solid will result in a more thermodynamically favored crystalline and stable structure. Further, in order to prevent the crystallization of the nucleated apatite, it may be preferred to introduce the calcium and phosphate ions separately into solution in a controlled manner. For example, the calcium and phosphate ions may be introduced into a solution of appropriate temperature and pH by titration, thereby limiting the amount of calcium phosphate formed. The use of highly concentrated or near supersaturation solutions also ensures a more rapid reaction. Preferred calcium ion sources include $Ca(NO_3)_2$, $CaCO_3$, $CaCl_2$ and calcium acetate $(Ca(CH_3COO)_2)$. Preferred phosphate ion sources include $Na_2HPO_4$, $KH_2PO_4$, $NaH_2PO_4$, $K_2HPO_4$, $NH_4H_2PO_4$ and $(NH_4)_2HPO_4$. Although the reaction can be carried out at ambient or sub-ambient temperatures, temperatures of near boiling point to increase the concentration of one reactant is a possible means of increasing the rate of reaction.

Once the precipitate has been formed, it is collected from the mother liquor as indicated in step 12 of FIG. 1. Collection may be carried out by any conventional method, including but not limited to filtration, centrifugation and sedimentation. A preferred method of collection is filtration and which affords a cake-like amorphous gel. Subsequent to or concurrent with the collection step, the gel may be washed to remove traces of the mother liquor including any unreacted solution ions as is illustrated in step 14 of FIG. 1. The material preferably may be washed with distilled water until the filtrate is ion-free.

In order to prepare the block solid calcium phosphate apatite of the present invention, the collected gel then is cast into hydrophobic molds, as is illustrated in step 16 of FIG. 1. In order to facilitate the mold filling step, additional water (5 to 80 wt %) may be added to the cake-like calcium phosphate gel with stirring or mixing to obtain a pourable consistency. The mold is filled and entrapped gases (air bubbles) are preferably removed. This may be accomplished by sonication or reducing pressure. The mold is preferably non-adhering to the gel. The mold may be made of polytetrafluoroethylene PTFE). Easy release of the gel from the mold helps prevent cracking and formation of internal stresses during drying. The reduction of stresses and cracking in the casting is desirable when forming a solid block product of high strength. When it is intended to grind the product material into a granular form, additional steps to prevent cracking may not be required. It also has been observed that mold geometry and size plays a role in minimizing cracking during drying. Larger molds and molds without high release coatings, tend to crack and degrade the mechanical strength of the resultant calcium phosphate apatite block solid.

A ceramic-like calcium phosphate apatite block solid material is obtained by dehydration and reactive association of the molded calcium phosphate gel, the surface of which is strongly interacting. The calcium phosphate gel is still reactive at this stage and will react to form a calcium phosphate apatite solid. To this effect, the gel is dehydrated slowly at low temperature in the range of 0° C. to 50° C. and preferably 4° C. to 37° C. and in controlled humidity, as is illustrated in step 17 of FIG. 1. The humidity is maintained in the range of about 55% to about 99% RH at the selected temperature. Humidity is controlled using conventional techniques and commercially available humidity chambers. It also has been observed that ambient conditions may be used in environments where ambient humidity and/or temperature do no fluctuate significantly.

Rate of dehydration and reaction is desirably controlled to prevent large scale crystallization at this point. The process is carried out over a period of weeks up to about a year. Longer reaction/dehydration times are associated with increased density and mechanical strength in the calcium phosphate apatite block solid. Thus, lower temperatures and higher relative humidity are generally favored in the process because they increase drying, and hence reaction, time. While drying can occur over a period of one to three days, the product is generally unsatisfactory because of cracking which weakens the mechanical strength. Drying times of more than one week are preferred.

The resulting low crystallinity calcium phosphate apatite block solid is a highly reactive, high strength material. The material may be machined into a desired shape, thus making the material readily adaptable for use as an implant device. High reactivity suggests high bioresorbability. The calcium phosphate apatite block solid of the present invention possesses a hardness and microporosity comparable to conventional ranges found to be acceptable for implant materials. Average porosity is in the range of about 30 to 100 Å. Hardness is in the range of about 20–40 VHN. The block solid is of higher strength and hardness than pressed powder compacts. Further, conventional pressed powder compacts do not keep their strength without high temperature treatments, which alter the composition and crystallinity of the compact.

If desired, the block solid may be ground to obtain a low crystallinity calcium phosphate apatite powder. Powders having a particle size in the range of about 250 µm to about 0.5 mm are contemplated.

Figure 2:
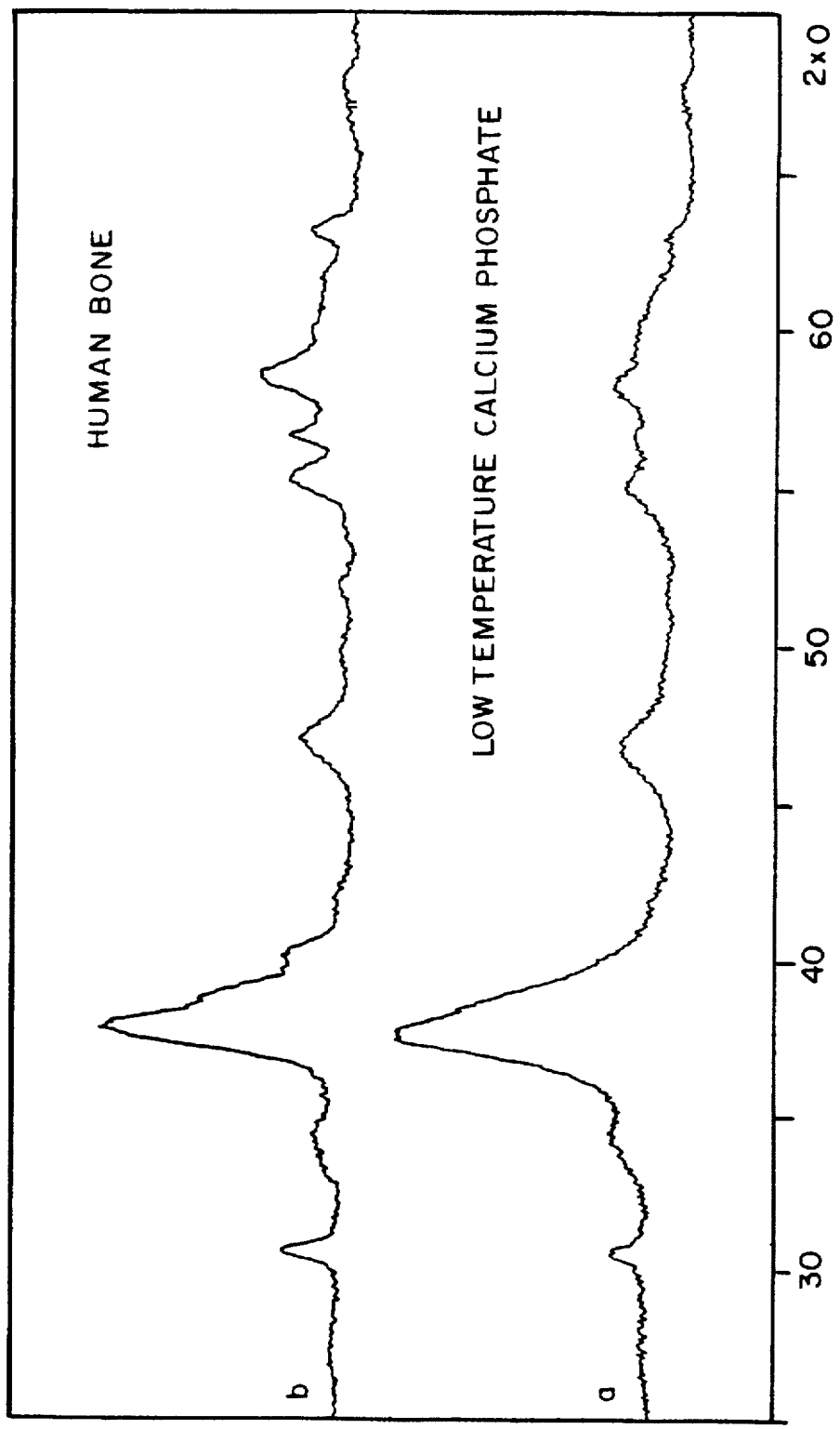
FIG. 2 is an x-ray diffraction pattern of (a) a calcium phosphate apatite solid prepared according to the invention and (b) human bone.

The resultant calcium phosphate apatite block solid closely approximates both the composition and crystallinity of natural bone. FIG. 2 depicts an X-ray diffraction (XRD) pattern of (a) naturally-occurring human bone and (b) the calcium phosphate apatite solid prepared according to the invention. By comparison of the two XRD patterns, it is apparent that the calcium phosphate apatite closely resembles human bone both in the degree of crystallinity (as indicated by the sharpness of the XRD peaks) and in composition (as indicated by peak position and intensity).

In a preferred embodiment of the invention, the precipitate is optionally matured before slow dehydration as shown in optional step 18 of FIG. 1. Maturation involves contact of the precipitate with an aqueous solution for a period of time under controlled conditions. The solution is typically distilled water, although ionic solutions may be used, such as calcium-, carbonate- or phosphate- containing solutions. The maturation is aimed at bulk and surface transformations of the gel nanocrystals and a regulation of their size in order to obtain ultimately a ceramic with the required porosity and composition. Maturation is a process which is similar to the aging of bone. During precipitation and maturation when carbonate is present in the mother solution, carbonate may enter the apatite structure and different apatites compositions corresponding to young or old bone mineral may be obtained. Thus, maturation affects the reactivity and the composition of the calcium phosphate gel.

Maturation is associated with an increase of crystallinity, a decrease of the labile phosphate environments and an increase in carbonate environments. In general, the longer the maturation time, the greater the increase in crystal size and the greater the decrease in surface reactivity of the calcium phosphate material. Also, as maturation progresses, carbonate content of the material increases and $HPO_4^{2-}$ content of the material decreases.

Maturation may occur for a time in the range of about one hour up to about one year. The length of maturation may be selected to obtain a calcium phosphate apatite approaching the composition of a particular aged bone. For example, it has been observed that maturation for about two to three days results in a calcium phosphate apatite having a composition similar to a child's bone. Similarly, maturation at one to six months and six to twelve months results in a product similar in composition to adult bone and elderly bone, respectively. The presence or absence of an inhibitor (see below) will also affect the preferred maturation time.

In another preferred embodiment of the present invention, a method is provided for inhibiting crystal growth after initial nucleation. An additive which inhibits the continued growth of apatite crystals is added to the precipitation solution as is shown in optional step 19 in FIG. 1. Typical inhibitors useful in the method of the invention include, but are in no way limited to $Mg^{2+}$, carbonate and pyrophosphate ions. Magnesium ions desirably may be added to the calcium solution and/or pyrophosphate or carbonate ions may be added to the phosphate solution. The inhibitors may be used singly or in combination with one another. Other additives known to inhibit crystallization in the calcium phosphate system are within the contemplation of the present invention. Inhibitors are added in an amount effective to inhibit crystal growth of the calcium phosphate apatite. Typical amounts are in the range of about 0.5 wt % to about 30 wt % of the total dry weight of the calcium and phosphate sources. The effective amount of inhibitor will vary dependent upon the particular inhibitor used. For example, large amounts (30 wt %) of sodium bicarbonate ($NaHCO_3$) may be added, whereas lesser amounts of magnesium ion may be required to be effective.

Figure 3:
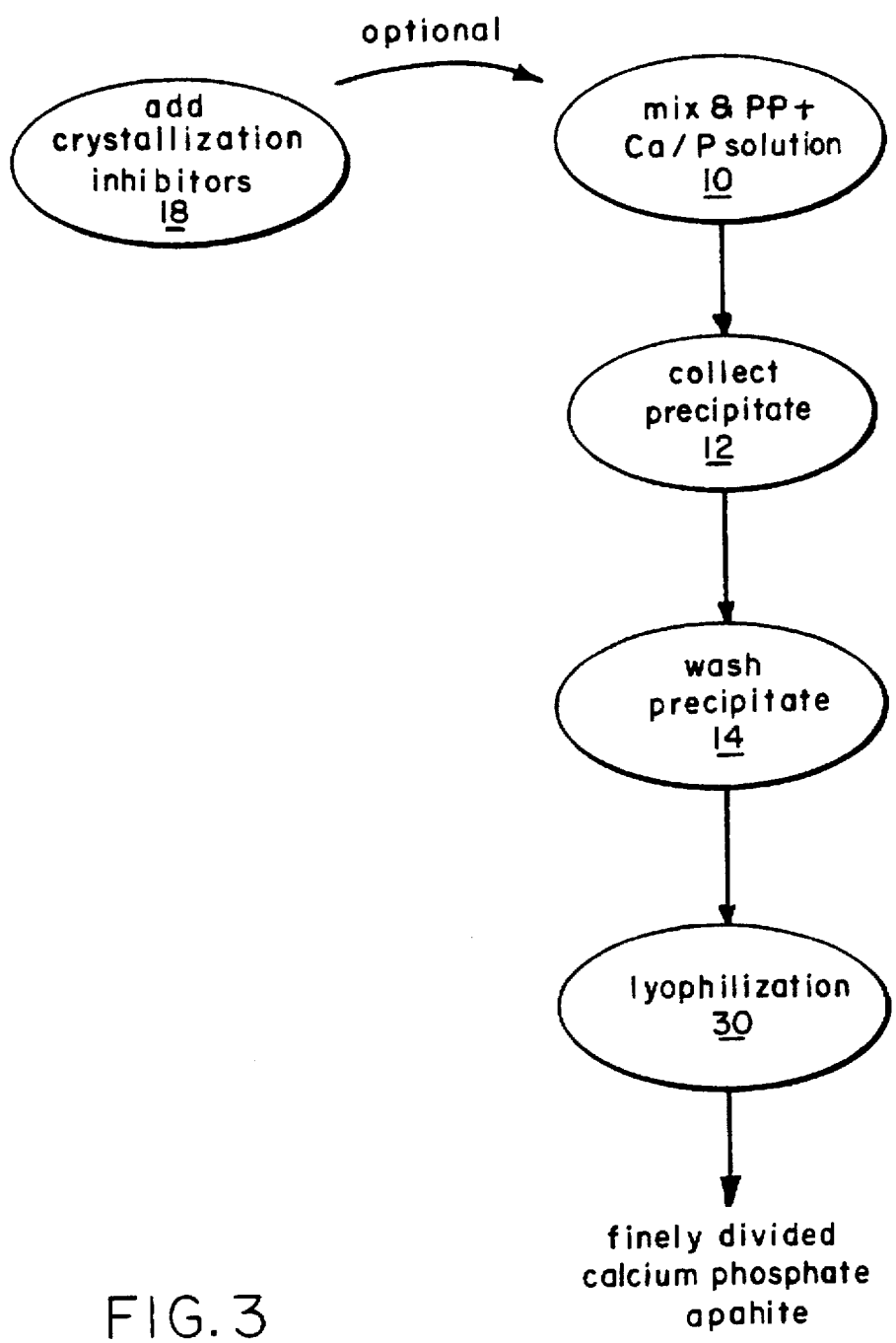
FIG. 3 is a block diagram illustrating another method of the invention.

In another method of the invention, the calcium phosphate apatite may be obtained as a finely divided powder. The method is described with reference to FIG. 3. Precipitation of a calcium phosphate solid as in step 10, collection of the precipitate from the mother liquor as in step 12 and washing of the solid as in step 14 are carried out as described above. A fine powder may be obtained by lyophilization of the precipitate at this point in the process as shown in step 30. Lyophilization is used because it permits the drying of the precipitate at low temperatures, so that no crystallization or further reaction occurs. Thus, the lyophilized powder retains the reactive sites and amorphous crystalline state of the precipitate.

According to the method of the invention, the calcium phosphate precipitate is collected and filtered immediately. It is preferred to perform this step in a cold room or at sub-ambient temperatures so as to preserve the low crystallinity state of the precipitate collected. Collection may typically be carried out by any conventional means, including, but in no way limited to gravity filtration, vacuum filtration, sedimentation or centrifugation. The collected precipitate is gelatinous and is washed more than once with distilled water, as described above. The washed precipitate is then immediately frozen, for example, but not limited to, by submerging into liquid nitrogen. Upon freezing, precipitate while kept frozen, is dried to remove the bulk of the entrained liquid. This procedure may be accomplished by placing the frozen precipitate into a vacuum chamber for a given period of time. Freeze-drying typically occurs at liquid nitrogen temperatures for a time in the range of 12–78 hrs, preferably about 24 hours, and under a vacuum in the range of $10^{-3}$–$10^{-5}$ torr. A preferred method includes lyophilization because the cryogenic temperatures typically used in lyophilization inhibit further crystallization of the material. As a result, the calcium phosphate apatite powder obtained thereby is an extremely fine free flowing powder.

In another embodiment, bioactive molecules may be added to the gel, as is illustrated in optional step 20 in FIG. 1. It is contemplated to incorporate bone regenerative proteins (BRP) into the calcium phosphate apatite powder or block solid. BRPs have been demonstrated to increase the rate of bone growth and accelerate bone healing. A bone graft including poorly crystalline calcium phosphate apatite and BRP is expected to promote bone healing even more rapidly than a bone graft using the calcium phosphate apatite of the present invention alone. The efficacy of BRP is further enhanced by controlling the solubility of the poorly crystalline calcium phosphate apatite such that it dissolves at a rate that delivers BRP, calcium, and phosphorus at the optimum dosage for bone growth. Such a method of incorporating BRP would include, but is not limited to, mixing a buffer solution for decomposition of calcium phosphate ions in step 10 containing BRP with its optimum pH that would maintain protein activity, instead of distilled water. Exemplary BRPs include, but are in no way limited to, Transforming Growth Factor-Beta, Cell-Attachment Factors, Endothelial Growth Factors, and Bone Morphogenetic Proteins. Such BRPs are currently being developed by Genetics Institute, Cambridge, Mass.; Genentech, Palo Alto, Calif.; and Creative Biomolecules, Hopkinton, Mass. Alernatively, BRP may be mixed with the calcium phosphate gel after filtration step 12.

It also is contemplated to incorporate antibiotics or their agents into the calcium phosphate apatite powder or solid. From a clinical sense, one of the major implication arising from a bone-graft surgery is a need to control the post-operative inflammation or infection. A bone graft including poorly crystalline calcium phosphate apatite and antibiotic (s) is expected to reduce the chances of local infection at the surgery site, contributing to infection-free, thus faster bone healing process. The efficacy of antibiotics is further enhanced by controlling the release of the poorly crystalline calcium phosphate apatite such that it dissolves at a rate that delivers antibiotic peptides or its active component at the most effective dosage to the tissue repair site. Exemplary antibiotics include, but are in no way limited to, penicillin, chlortetracycline hydrochloride (Aureomycine), chloramphenicol and oxytetracycline (Terramycine). Both antibiotics, mostly polypeptides, and bone regenerating proteins may be intermixed with the poorly crystalline calcium phosphate apatite material of the present invention, to locally deliver all or most of the necessary components in facilitating optimum condition for bone tissue repair.

Examples are provided as illustrative of the invention but are in no way intended to be construed as limiting of the invention.

EXAMPLE 1

This example illustrates the typical formation of a calcium phosphate apatite block solid according to the method of the invention.

Precipitation

A solution of 218 g of disodium hydrogen orthophosphate ($Na_2HPO_4$, $12H_2O$) in 1200 ml of distilled water and a solution of 70 g of calcium nitrate [$Ca(NO_3)_2$, $4H_2O$] in 500 ml of distilled water were prepared. The calcium solution was quickly poured into the phosphate solution at room temperature and with stirring. Precipitation was immediate and substantially complete. The pH of the precipitate is adjusted to 7.4 by the addition of sodium hydroxide solution in order avoid the formation of acidic calcium phosphates. The precipitate was separated immediately from its mother solution by filtration through a Buchner filter (with a total surface about 0.1 sq.m), and was washed by about 3 liters of distilled water. A gel cake of low crystallinity calcium phosphate is obtained on the filter paper.

Formation of ceramic-like block solid at low temperature

After filtration and washing, an appropriate amount of distilled water (5 to 80 weight %) was added to the gel precipitate. The gel was homogenized by whipping energetically for a few minutes. It was then cast into polytetrafluoroethylene (PTFE) molds (diameter 60 mm; height 22 mm), and sonicated for a few minutes in order to release the air bubbles trapped in the gel.

The molds were dried in chamber at controlled temperature (5° to 37° C.) and humidity (10 to 95% RH). The samples shrank slowly on drying and release most of their water. The rate of drying and the shrinkage of the samples depended on the initial water content. The material hardened on drying and became glassy. It contained about 10% of residual water. Dense pellet (60% of theoretical density of apatite), could be obtained.

The biaxial flexure stress value of the pellets was about 4 MPa, and about 20 VHN for the microhardness testing. The size of the micropores of the sample averaged 30 to 100 Å. These properties are comparable to ranges known to be acceptable for bone graft implants. A pore size of 30 to 100 Å is useful for protein absorption, cell fixation and multiplication.

EXAMPLES 2–4

These examples were carried out as described in Example 1 and illustrate the effect of different dehydration times on the hardness of the resultant calcium phosphate apatite block solid.

TABLE 1

Preparation of block solid apatite using varying drying times.

| No. | temperature (°C.) | relative humidity (%) | dehydration time (days) | hardness (VHN) |
|---|---|---|---|---|
| 2 | 4 | 85–95 | ~14 | 17 |
| 3 | 25 | 60–70 | ~8 | 17 |
| 4 | 50 | 20–30 | ~3 | microcracks |

It will be appreciated that the more rapid dehydration times resulted in deterioration of the block solid mechanical properties.

EXAMPLE 5

This example illustrates the typical formation of a calcium phosphate apatite block solid using inhibitors.

According to the method of preparation of Example 1, and in order to diminish the particle size of materials, and thus the pore size, several crystal growth inhibitors can be incorporated in the precipitation and maturation solution ($CO_3^{2-}$ ions, $Mg^{2+}$ ions, and $P_2O_7^{4-}$ ions) separately or simultaneously.

When adding $CO_3^{2-}$ ions, typically 80 g of sodium bicarbonate ($NaHCO_3$) was added to the phosphate solution. When adding $Mg^{2+}$ ions, typically 1.25 g of magnesium chloride ($MgCl_2 \cdot 6H_2O$) was added to the calcium ion solution. When adding $P_2O_7^{4-}$ ions, typically 1 g of sodium pyrophosphate ($Na_4P_2O_7 \cdot 10H_2O$) was added to phosphate solution.

The influence of these crystal growth inhibitors was apparent on the X-ray diffraction pattern. The bands were broader than for samples obtained in example 1 and characteristic of a very poor crystallinity.

IR spectrometry showed $CO_3^{2-}$ bands. Thus the carbonate had been incorporated into the calcium phosphate apatite product. The carbonate locations were analogous to those found in bone mineral. Two carbonate bands 873 and 879 $cm^{-1}$ were assigned respectively to type A and type B carbonate. A third carbonate bands at 866 $cm^{-1}$ was assigned to a labile carbonate species mainly on the surface of the powders. The specific surface area of the lyophilized crystals reached 120 sq.m $g^{-1}$.

The ceramic-like materials were obtained by the method described in example 1. The micropore size was 110 Å, the flexure stress value 3.5 MPa and the microhardness 35 VHN. In general, it was observed that use of inhibitors produced a solid block product with increased mechanical strength over solids obtained without inhibitors.

EXAMPLES 6–8

These examples were carried out as described in Example 5 and illustrate the effect of different inhibitors on the properties of the resultant calcium phosphate apatite block solid.

TABLE 2

Preparation of block solid apatite using different inhibitors.

| No. | inhibitor | inhibitor added (g) | crystal size (Å) | specific surface area (sq. m/g) | $CO_3^{2-}$ content (wt %) | hardness (VHN) |
|---|---|---|---|---|---|---|
| 6 | $CO_3^{2-}$ | $NaHCO_3$ (80) | 255 | 76 | 1.2 | 28.9 |
| 7 | $CO_3^{2-}$, $Mg^{2+}$ | $NaHCO_3$ (80), $MgCl_2 \cdot 6H_2O$ (1.25) | 200 | 80 | 1.5 | 30.4 |
| 8 | $CO_3^{2-}$, $Mg^{2+}$, $P_2O_7^{4-}$ | $NaHCO_3$ (80), $MgCl_2 \cdot 6H_2O$ (1.25) $Na_4P_2O_7 \cdot 10 H_2O$ (1) | 200 | 88 | 1.8 | 32.4 |

It is readily apparent that use of inhibitors resulted in an increase in hardness. Further, selection of various inhibitors allows for the selection of a desired hardness, carbonate content, crystal size and specific surface area. Note that these samples were not subject to maturation.

EXAMPLES 9–12

These examples were carried out as described in Example 5 and illustrate the effect of different inhibitors on the properties of the resultant calcium phosphate apatite block solid.

TABLE 3

Preparation of block solid apatite using varying maturation times.

| No. | maturation time (days) | specific surface area (sq. m/g) | Ca/P ratio | $CO_3^{2-}$ content (wt %) |
|---|---|---|---|---|
| 9 | 10 | 92 | 1.63 | 4.3 |
| 10 | 100 | 117 | 1.66 | 5.7 |
| 11 | 250 | 120 | 1.72 | 6.7 |

It is readily apparent that maturation significantly increases the carbonate content of the resultant calcium phosphate apatite solid block. These results further demonstrate the ability to alter the calcium/phosphate ratio as desired.

EXAMPLE 12

This example illustrates the formation of a calcium phosphate apatite finely divided powder according to the method of the invention.

Calcium and phosphate ion solutions were prepared and combined as in Example 1. The precipitate was collected and washed as in Example 1.

After collection and before drying, the recovered solid was lyophilized to a free flowing solid and the particle size and the chemical composition was investigated. Chemical analysis gave a Ca/P=1.45, characteristic of a non- stoichiometric apatite phase.

X-ray diffraction of the lyophilized powder shows a poor crystallinity, with the appearance of wide peaks analogous to those found in bone mineral. One can identify the peaks 211, 002, 310, 222, and 213 of the apatite structure. The particle observed by transmission electron microscopy were elongated plate-like crystals with irregular shaped (average length of about 300 Å).

IR spectrometry shows that the spectrum of synthetic apatite and that of bone mineral are analogous, with the absorption bands due to $PO_4^{3-}$ in apatitic environment. In addition, non-apatitic labile environments analogous to those found in bone mineral are observed at 610 and 530 $cm^{-1}$. This last band is due to $HPO_4$ ions.

The specific surface area was about 100 sq.m/g, similar to that estimated for bone mineral crystals. Mercury porosimetry showed a homogeneous micropore distribution, with an average pore diameter about 30 to 100 Å. This microporosity seems favorable for protein incorporation (see, below).

EXAMPLE 13

This example illustrates maturation of the precipitate in order to obtain a carbonate apatite close in opposition to bone material.

Carbonate ions are the third major constituent of bone mineral. The maturation allowed the preparation of carbonated apatites with characteristics closer to those of bone material.

The precipitate obtained according the example 2 was left to mature in the mother solution for various periods of time ranging from 1 hour to 1 year. The amount of carbonate ions taken up just after precipitation was very low (1–2%) and most of the carbonate ions were incorporated during maturation of the precipitate in the mother solution (6% carbonate at 1 month). The carbonate ions were occupying the same site as in bone mineral. The incorporation of carbonate ions was associated to a decrease of the $HPO_4^{2-}$ content, an increase of the crystallinity of the apatite and a decrease of the amount of labile non-apatitic environments. The samples obtained after one month maturation were similar to human bone mineral.

These samples gave solid materials according to the process described in example 1. They were characterized by a flexure strength of 2.5 MPa, a microhardness of 25 VHN, and a micropore size averaging 105 Å (with 3 inhibitors and 100 days of maturation times).

EXAMPLE 14

This example illustrates the incorporation of a protein into they calcium phosphate apatite block solid.

According to the method of preparation of Example 1, various amounts of bovine serum albumin were incorporated into the apatite gel at a ratio of albumin/ (albumin+apatite) ranging from 0.5 to 50 wt %.

After whipping, the ceramic was prepared following the method of Example 1. Concerning the sample with the highest albumin concentration (50%), about 8% was released within 50 hours after immersion of the pellet in water. The remaining (42%) could only be released by total dissolution of the ceramic in acidic media.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

What is claimed is:

1. A method of preparing a low crystallinity calcium phosphate apatite, comprising:

precipitating a low crystallinity calcium phosphate from an aqueous solution comprising calcium and phosphate ions;

collecting the low crystallinity calcium phosphate from the solution; and dehydrating the low crystallinity calcium phosphate in a relative humidity of less than 100% and at a temperature to obtain a low crystallinity calcium phosphate apatite block solid.

2. The method of claim 1, further comprising:

casting the low crystallinity calcium phosphate into a mold before dehydration.

3. The method of claim 1, wherein the aqueous solution is selected to provide a calcium to phosphate ratio in the range of about 1.3 to 1.7.

4. The method of claim 1, wherein the aqueous solution is selected to provide a calcium to phosphate ratio in the range of about 1.5 to 1.68.

5. The method of claim 1, wherein the precipitation is carried out in the aqueous solution further comprising carbonate ions.

6. The method of claim 1, wherein the aqueous solution is at a pH in the range of about 6.0 to about 8.5.

7. The method of claim 1, wherein the aqueous solution is at a pH in the range of about 7.3 to about 7.5.

8. The method of claim 1, wherein the calcium and phosphate ions are introduced into the aqueous solution by fast_addition.

9. The method of claim 1, wherein the calcium and phosphates ions are introduced into the aqueous solution by titration.

10. The method of claim 1, wherein the step of collection is selected from the group consisting of filtration, centrifugation and sedimentation.

11. The method of claim 1, wherein the aqueous solution further comprises a crystallization inhibitor.

12. The method of claim 11 wherein the inhibitor is present in a range of about 0.5 wt % to about 30 % wt total dry weight of calcium and phosphate ion sources.

13. The method of claim 11, wherein the inhibitor is selected from the group consisting of carbonate ion, magnesium ion, and pyrophosphate ion.

14. The method of claim 1 or 11, further comprising:

maturing the low crystallinity calcium phosphate in the aqueous solution prior to collection.

15. The method of claim 14, wherein maturation is carried out for a time sufficient to obtain a calcium phosphate gel having a composition substantially similar to child's bone.

16. The method of claim 14, wherein maturation is carried out for a time sufficient to obtain a calcium phosphate gel having a composition substantially similar to adult's bone.

17. The method of claim 14, wherein maturation is carried out for a time sufficient to obtain a calcium phosphate gel having a composition substantially similar to elderly bone.

18. The method of claim 14, wherein the calcium phosphate apatite is matured for a time in the range of about one hour to about one year.

19. The method of claim 14, wherein the calcium phosphate apatite is matured for a time in the range of about two weeks to about six months.

20. The method of claim 1 or 11, wherein the step of dehydration is carried out at a temperature in the range of about 1° C. to about 50° C.

21. The method of claim 14, wherein the step of dehydration is carried out at a temperature in the range of about 1° C. to about 50° C.

22. The method of claim 1, wherein the step of dehydration is carried out at a temperature in the range of about 4° C. to about 37° C.

23. The method of claim 1 or 11, wherein the step of dehydrating the low crystallinity calcium phosphate comprises dehydrating in a humidity controlled to within the range of about 55% to about 99% RH at a temperature of less than 50° C.

24. The method of claim 14, wherein the step of dehydrating the low crystallinity calcium phosphate comprises dehydrating in a humidity controlled to within the range of about 55% to about 99% RH at a temperature of less than 50° C.

25. The method of claim 1 or 11, wherein the step of dehydrating the low crystallinity calcium phosphate comprises dehydrating in a humidity controlled to within the range of about 60% to about 70% RH at 25° C.

26. The method of claim 1 or 11, wherein step of dehydration is carried out for a time in the range of about one week to about one year.

27. The method of claim 14, wherein step of dehydration is carried out for a time in the range of about one week to about one year.

28. The method of claim 1 or 11, wherein step of dehydration is carried out for a time in the range of about two weeks to about six months.

29. The method of claim 1 or 11, wherein step of dehydration is carried out for a time in the range of about three weeks to about four weeks.

30. The method of claim 1, further comprising the step of including a bioactive molecule into the calcium phosphate apatite.

31. The method of claim 30, wherein the bioactive molecule is added to the collected precipitate before dehydration.

32. The method of claim 30, wherein the bioactive molecule is added to the aqueous solution.

33. The method of claim 30, wherein the bioactive molecule is selected from the group consisting of bone regenerative proteins, and antibiotics and its agents.

34. A method of preparing a low crystallinity calcium phosphate apatite, comprising precipitating a low crystalline calcium phosphate from an aqueous solution comprising calcium and phosphate ions;

collecting the low crystallinity calcium phosphate from the solution; and lyophilizing the collected precipitate to obtain a low crystallinity calcium phosphate apatite.

35. A low crystallinity calcium phosphate apatite block solid prepared according to the method of claim 1, 11 or 30.

36. A low crystallinity calcium phosphate apatite block solid prepared according to the method of claim 14.

37. The low crystallinity calcium phosphate apatite block solid of claim 35, further characterized by having a porosity in the range of about 30 Å to about 100 Å.

38. The low crystallinity calcium phosphate apatite block solid of claim 35, further characterized by having a hardness in the range of about 20 VHN to about 40 VHN.

39. The low crystallinity calcium phosphate apatite block solid of claim 36, further characterized by having a porosity in the range of about 30 Å to about 100 Å.

40. The low crystallinity calcium phosphate apatite block solid of claim 36, further characterized by having a hardness in the range of about 20 VHN to about 40 VHN.

41. A low crystallinity calcium phosphate apatite characterized as a solid block material having a porosity in the range of about 30 Å to about 100 Å and a hardness in the range of about 20 VHN to about 40 VHN.

* * * * *